United States Patent
Yu et al.

(10) Patent No.: US 10,308,684 B2
(45) Date of Patent: Jun. 4, 2019

(54) CELL PENETRATING STAPLED PEPTIDE, MANUFACTURING METHOD THEREFOR, AND USE THEREOF

(71) Applicant: SEOUL NATIONAL UNIVERSITY R&DB FOUNDATION, Seoul (KR)

(72) Inventors: Jaehoon Yu, Gyeonggi-do (KR); Soonsil Hyun, Seoul (KR); Yan Lee, Seoul (KR); Seonju Lee, Chungcheongbuk-do (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 15/529,967

(22) PCT Filed: Nov. 27, 2015

(86) PCT No.: PCT/KR2015/012807
§ 371 (c)(1),
(2) Date: May 25, 2017

(87) PCT Pub. No.: WO2016/085280
PCT Pub. Date: Jun. 2, 2016

(65) Prior Publication Data
US 2017/0342108 A1 Nov. 30, 2017

(30) Foreign Application Priority Data
Nov. 28, 2014 (KR) .......................... 10-2014-0168937

(51) Int. Cl.
| | |
|---|---|
| A61K 38/10 | (2006.01) |
| A61K 38/16 | (2006.01) |
| A61K 38/00 | (2006.01) |
| A61K 38/04 | (2006.01) |
| C07K 5/00 | (2006.01) |
| C07K 7/00 | (2006.01) |
| C07K 16/00 | (2006.01) |
| C07K 17/00 | (2006.01) |
| C07K 7/08 | (2006.01) |
| A61K 47/42 | (2017.01) |
| A61K 47/64 | (2017.01) |
| A61K 31/713 | (2006.01) |
| C07K 1/107 | (2006.01) |
| C12N 15/113 | (2010.01) |
| C07K 1/113 | (2006.01) |
| C07K 14/00 | (2006.01) |
| A61K 38/12 | (2006.01) |

(52) U.S. Cl.
CPC .............. *C07K 7/08* (2013.01); *A61K 31/713* (2013.01); *A61K 38/10* (2013.01); *A61K 38/12* (2013.01); *A61K 47/42* (2013.01); *A61K 47/64* (2017.08); *A61K 47/6455* (2017.08); *C07K 1/1075* (2013.01); *C07K 1/1077* (2013.01); *C07K 1/113* (2013.01); *C07K 14/001* (2013.01); *C12N 15/113* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| | | |
|---|---|---|
| 2010/0093086 A1 | 4/2010 | Lin et al. |
| 2010/0129341 A1 | 5/2010 | Sakon et al. |
| 2016/0229894 A1* | 8/2016 | Yu ............................. C07K 7/08 |

FOREIGN PATENT DOCUMENTS

| | | | |
|---|---|---|---|
| WO | 2005044839 A2 | 5/2005 | |
| WO | 2008045238 A2 | 4/2008 | |
| WO | 2013150338 A1 | 10/2013 | |
| WO | WO-2014052647 A2 * | 4/2014 | ............... C07K 7/56 |
| WO | 2015057009 A1 | 4/2015 | |

OTHER PUBLICATIONS

Amand et al., Biochem. Biophys. Res. Comm. 418:569-474 (2012) (Year: 2012).*
Madani et al., J. Biophys.2011:1-10 (2011) (Year: 2011).*
Munyendo et al., Biomolecules 2:187-202 (2012) (Year: 2012).*
Chu, Q., et al., "Towards understanding cell penetration by stapled peptides", "Med. Chem. Commun.", Sep. 11, 2014, pp. 111-119, vol. 6.
Kim, Y.-W., et al., "Synthesis of all-hydrocarbon stapled a-helical peptides by ring-closing olefin metathesis", "Nature Protocols", May 12, 2011, pp. 761-771, vol. 6, No. 6.

* cited by examiner

*Primary Examiner* — James H Alstrum-Acevedo
*Assistant Examiner* — Thea D'Ambrosio
(74) *Attorney, Agent, or Firm* — Hultquist, PLLC; Steven J. Hultquist

(57) ABSTRACT

The present invention relates to a stapled peptide, a preparation method thereof and the use thereof, and more specifically to an amphipathic alpha-helical stapled peptide comprising hydrophobic amino acids and hydrophilic amino acids, a preparation method thereof, and the use thereof for intracellular delivery of an active substance.

6 Claims, 13 Drawing Sheets
(12 of 13 Drawing Sheet(s) Filed in Color)
Specification includes a Sequence Listing.

CELL PENETRATING STAPLED PEPTIDE, MANUFACTURING METHOD THEREFOR, AND USE THEREOF

CROSS-REFERENCE TO RELATED APPLICATIONS

This application is a U.S. national phase under the provisions of 35 U.S.C. § 371 of International Patent Application No. PCT/KR2015/012807 filed Nov. 27, 2015, which in turn claims priority of Korean Patent Application No. 10-2014-0168937 filed Nov. 28, 2014. The disclosures of such international patent application and Korean priority patent application are hereby incorporated herein by reference in their respective entireties, for all purposes.

TECHNICAL FIELD

The present invention relates to a stapled peptide, a method for preparing the same and the use thereof, and more specifically to an amphipathic alpha-helical stapled peptide comprising hydrophobic amino acids and hydrophilic amino acids, a method for preparing the same, and the use thereof for intracellular delivery of an active substance.

BACKGROUND ART

Typical known examples of cell-penetrating peptides (CPPs) include TAT peptides, penetratin peptides, and artificially synthesized peptides comprising 7 to 9 arginine residues. It is known that these peptides are rich in arginine, easily recognize negatively charged substances on the cell surface, and enter cells by endocytotic mechanism.

Such cell-penetrating peptides have been used for intracellular delivery of substances that are difficult to deliver intracellularly, including large molecular substances such as proteins or nucleic acids, and even small molecules. However, such conventional peptides require micromolar concentrations to exhibit a sufficient ability to penetrate cells. These cell-penetrating peptides need to be covalently conjugated to the substance to be delivered into cells in order to increase the cell-penetrating ability of the substance. Thus, these peptides have insufficient efficiency. This is because physiologically active substances (such as proteins or small molecules) to be delivered into cells mostly perform their function at concentrations lower than micromolar concentrations. Thus, efforts have been made to develop a technology that enables cell-penetrating peptides to penetrate cells with high efficiency at lower concentrations.

In recent years, efforts have been made to prepare a stapled peptide from a portion of a physiologically active protein in order to regulate the physiological activity thereof. Such stapled peptides for regulating physiological activity mostly consist of hydrophobic amino acids. This is because amino acids playing an important role in protein-protein interactions consist mainly of hydrophobic functional groups.

Recently, the inventors of the application prepared a peptide multimer comprising covalent linkages at two or more amino acid positions of amphipathic alpha-helical peptides comprising hydrophilic and hydrophobic amino acids (PCT/KR2014/009778). It was found that this peptide multimer can be used as a cell-penetrating peptide. Particularly, as described in PCT/KR2014/009778, the present inventors previously prepared dimeric peptides by introducing cysteine instead of leucine into some hydrophobic residues of amphipathic peptides and connecting the peptides by two disulfide bonds. It was found that such dimeric peptides have a greatly increased alpha-helical content, are chemically stable, and have a cell-penetrating ability which is about 500-fold higher than conventional CPPs.

However, if one peptide of a dimeric peptide has 16 amino acid residues, the dimeric peptide consists of 32 amino acids. Thus, in order to develop a better cell-penetrating peptide, it is required to prepare a stapled peptide and compare the cell-penetrating ability thereof with that of a dimeric peptide.

Under this technical background, the present inventors have found that, based on a stapled peptide, a cell-penetrating peptide that is a peptide monomer can be prepared which has an improved cell-penetrating ability while maintaining its chemical stability, thereby completing the present invention.

DISCLOSURE OF INVENTION

Technical Problem

It is an object of the present invention to provide an amphipathic alpha-helical stapled peptide which can efficiently penetrate cells while having a smaller number of amino acids compared to conventional cell-penetrating peptides, a preparation method thereof, and the use thereof.

Technical Solution

To achieve the above object, the present invention provides an amphipathic alpha-helical stapled peptide comprising hydrophobic amino acids and hydrophilic amino acids, wherein two or more amino acids of the peptide are connected to each other. The amino acid may comprise one or more hydrophilic amino acids selected from the group consisting of arginine, lysine, and histidine, or one or more hydrophobic amino acids selected from the group consisting of leucine, valine, tryptophan, phenylalanine, tyrosine, and isoleucine.

The present invention also provides a method for preparing a stapled peptide, comprising the steps of: preparing a plurality of amino acids functionalized with double bond-containing compounds; and connecting at least two amino acids to each other by a reaction between the double bond-containing compounds of the amino acids arranged at predetermined positions.

The present invention also provides a composition for intracellular delivery of a biologically active substance, which comprises the above-described stapled peptide and the biologically active substance.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 9a shows HPLC analysis results for 5-TAMRA labeled stAK; FIG. 9b shows HPLC analysis results for 5-TAMRA labeled stBK; FIG. 9c shows HPLC analysis results for 5-TAMRA labeled stCK; FIG. 9d shows HPLC analysis results for 5-TAMRA labeled stDK; and FIG. 9e shows HPLC analysis results for 5-TAMRA labeled stEK.

FIG. 10a shows MALDI-TOF mass spectrometry results for 5-TAMRA labeled stAK; FIG. 10b shows MALDI-TOF mass spectrometry results for 5-TAMRA labeled stBK; FIG. 10c shows MALDI-TOF mass spectrometry results for 5-TAMRA labeled stCK; FIG. 10d shows MALDI-TOF mass spectrometry results for 5-TAMRA labeled stDK; and FIG. 10e shows MALDI-TOF mass spectrometry results for 5-TAMRA labeled stEK.

BEST MODE FOR CARRYING OUT THE INVENTION

Figure 1:
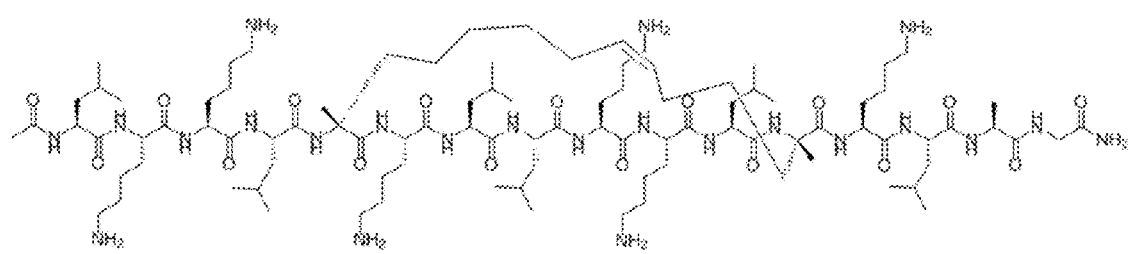
FIG. 1 shows the chemical structure of stCK that is an example of an amphipathic alpha-helical stapled peptide.

In one aspect, the present invention relates to an amphipathic alpha-helical stapled peptide comprising hydrophobic amino acids and hydrophilic amino acids, wherein two or more amino acids of the peptide are connected to each other.

As used herein, the term "stapled peptide" means that peptide regions are connected to each other. In one embodiment, in order to increase the chemical stability of alpha-helices, the i position and i+4 position (or i+7 and i+11 positions) of the alpha-helix can be stapled using various covalent bonding methods. Specifically, the amino acids at one or more positions selected from the group consisting of i, i+3, i+4, i+7, i+8, i+10 and i+11 (where i is an integer) may be stapled Amino acids may be stapled by a covalent bond to thereby increase the cell-penetrating ability. In some cases, two or more amino acid positions selected from the group consisting of i, i+3, i+4, i+7, i+8, i+10 and i+11 (where i is an integer) may be stapled.

Typically, two amino acids may be connected to each other by a disulfide bond, a carbon-carbon double bond or an amide bond. Examples of the method for linking two amino acids to each other include introduction of disulfide between two amino acid positions, introduction of a carbon-carbon double bond by a metathesis reaction, introduction of an amide bond, introduction of a short linker by the Michael reaction, and the like. Such stapling makes it highly possible to prepare a cell-penetrating peptide having an improved cell-penetrating ability and desired chemical stability.

If a peptide is alpha-helical, two or more amino acids of the peptide can be connected to each other by a compound having a cyclic ring structure. The size of the cyclic ring may vary depending on the amino acid number of the alpha-helical peptide. One or more staples may be contained in the peptide.

In a particular embodiment of the present invention, one or more amino acids of the peptide may be functionalized with a double bond-containing compound. For example, amino acids can be connected to each other by a ring structure produced by a ring-closing metathesis between double bond-containing compounds. The functionalized amino acids may be amino acids substituted with an alkenyl side-chain. The alkenyl side-chain may be one or more selected from the group consisting of pentenyl, hexenyl, heptenyl, octenyl, nonenyl, decenyl, undecenyl and dodecenyl groups.

The amino acids of the peptide are not specifically limited as long as they can maintain the α-helical structure while showing amphipathic properties. For example, the hydrophilic amino acid may be one or more selected from the group consisting of arginine, lysine, and histidine, and the hydrophobic amino acid may be one or more selected from the group consisting of leucine, valine, tryptophan, phenylalanine, tyrosine, and isoleucine.

Specifically, in an example of the present invention, an amphipathic alpha-helical stapled peptide consisting of lysine and leucine residues was prepared, and the cell-penetrating ability thereof was compared to those of an already known non-stapled peptide and an already known cell-penetrating peptide. As a result, it was shown that the stapled peptide according to the present invention exhibited an excellent ability to penetrate cells.

In some embodiments, the peptide may further comprise histidine in order to increase the efficiency of intracellular delivery. Histidine can act in endosomal escape after intracellular delivery. For example, the peptide may contain three histidine residues at the lysine position. Where the peptide contains one or more histidine residues at the lysine position, the efficiency of intracellular delivery of the peptide can be increased.

In other embodiments, the peptide may further comprise cysteine at N-terminus or C-terminus of the peptide. The efficiency of delivery of a substance to be delivered may change depending on the position of cysteine in the peptide. For example, the properties of the substance to be delivered may change. Where the substance to be delivered is a negatively charged substance, cysteine may be located at the N-terminus of the peptide to increase the alpha-helical content of the peptide, thereby increasing the efficiency of delivery of the substance. Where the substance to be delivered is a positively charged substance, cysteine may be located at the C-terminus of the peptide to increase the alpha-helical content of the peptide, thereby increasing the efficiency of delivery of the substance.

Additionally, a separate linker may also be introduced between the peptide and the cysteine added at the N-terminus or C-terminus. The linker may comprise one or more, for example, one to three glycine or alanine residues. The physical properties or delivery efficiency of the peptide may change depending on the length or kind of linker, and may also change depending on a particular substance to be delivered.

The number of amino acids contained in the peptide is not particularly limited as long as an alpha-helical structure that is a stable secondary structure can be formed. For example, the peptide may contain 5-20 amino acids. The present inventors have found that the cell-penetrating ability of the stapled peptide according to the present invention compares favorably with that of a previously developed cell-penetrating peptide (CPP) having 24 to 32 amino acids while the peptide of the present invention has a small number of amino acids (for example, 16 amino acids) compared to the previous cell-penetrating peptide. Thus, according to the present invention, a highly useful cell-penetrating peptide can be prepared in a cost-effective manner In order to collect the amine groups of the hydrophilic amino acids to one side of the α-helical peptide, one to three hydrophilic amino acids may be alternately arranged, and the remaining sequence may comprise one to three alternately arranged hydrophobic amino acids. For example, one to three hydrophilic amino acids may be arranged alternately with one to three hydrophobic amino acids, and thus at least one of the i+3 and i+4 positions of the amphipathic peptide may comprise an amino acid having the same polarity as that at the i position.

Specifically, the stapled peptide may comprise any one of the following sequences, and is one produced by introducing the carbon-carbon double bond through a metathesis reaction. In the following sequences, $R_8$ denotes (R)-2-(7'-octenyl) alanine, and $S_5$ denotes (S)-2-(4'-pentenyl) alanine:

$R_8$KKLLKLS$_5$KKLLKLAG (SEQ ID NO: 1)

LKKR$_8$LKLLKKS$_5$LKLAG (SEQ ID NO: 2)

LKKLR$_8$KLLKKLS$_5$KLAG (SEQ ID NO: 3)

LKKLLKR$_8$LKKLLKS$_5$AG (SEQ ID NO: 4)

LKKLLKLR$_8$KKLLKLS$_5$G (SEQ ID NO: 5)

LKKLLKLLR$_8$KLLKLAS$_5$ (SEQ ID NO: 6)

LKHLLHLR$_8$KHLLKLS$_5$G (SEQ ID NO: 7)

CLKKLLKLR$_8$KKLLKLS$_5$G. (SEQ ID NO: 8)

The stapled peptide according to the present invention has an excellent ability to penetrate cells, and thus can exhibit a desired cell-penetrating ability even when it is used at the minimum concentration. Accordingly, the stapled peptide according to the present invention can exhibit excellent intracellular delivery ability, and can also achieve a desired effect even when a low concentration of a biologically active substance is used.

A peptide multimer having the ability to efficiently penetrate cells even at low concentration (low nM) was previously prepared by the present inventors. However, this peptide multimer comprises about 24 to 32 amino acids. The cell-penetrating ability of a peptide does not necessarily increase in proportion to the amino acid number (or length) of the peptide. Thus, if the cell-penetrating ability of a peptide compares favorably with that of the cell-penetrating peptide (previously prepared by the present inventors) having 24 to 32 amino acids while the peptide has a small number of amino acids (for example, 16 amino acids) compared to the previous cell-penetrating peptide, the peptide is highly useful and can be prepared in a cost-effective manner Therefore, the present invention is intended to provide a cell-penetrating peptide for intracellular delivery of a biologically active substance, which contains a reduced number of amino acids.

The present inventors have conducted studies on the general properties of cell-penetrating peptides, and as a result, have reached a conclusion that increasing the alpha-helical content of the peptide has a close relation with the cell-penetrating ability of the peptide (of course, the alpha-helical content is not a necessary and sufficient condition for the cell-penetrating condition). The present invention aims at preparing a stapled peptide based on the amphipathic alpha-helical peptide previously developed by the present inventors in order to increase the cell-penetrating ability of the peptide.

Therefore, in another aspect, the present invention is directed to a composition for intracellular delivery of a biologically active substance, which comprises the above-described stapled peptide and the biologically active substance.

The biologically active substance, a kind of cargo, may be a substance that binds to the cellular transmembrane domain so as to be delivered to the cell to thereby regulate any physiological phenomena in vivo. For example, the biologically active substance may be DNA, RNA, siRNA, an aptamer, a protein, an antibody or a cytotoxic compound, but is not limited thereto.

In addition, a substance for regulating biological activity or function or other delivery carrier may additionally be bound to the stapled peptide according to the present invention. In this case, the peptide and the substance for regulating biological activity or function or other delivery carrier can form a complex structure. The substance or delivery carrier may be connected to the stapled peptide by, for example, a non-covalent bond or a covalent bond. The non-covalent bond may be one or more selected from the group consisting of, for example, a hydrogen bond, an electrostatic interaction, a hydrophobic interaction, a van der Waals interaction, a pi-pi interaction, and a cation-pi interaction. The covalent bond may be either a degradable bond or a non-degradable bond. The degradable bond may be a disulfide bond, an acid-degradable bond, an ester bond, an anhydride bond, a biodegradable bond, or an enzyme-degradable bond, but is not limited thereto. The non-degradable bond may be either an amide bond or a phosphate bond, but is not limited thereto.

The cytotoxic compound can be connected to the peptide by a non-covalent bond such as an electrostatic bond or a host-guest bond. For example, the cytotoxic compound may be doxorubicin, Methotrexate, Paclitaxel, Cisplatin, Bleomycin, taxol, berberine or curcumin, but is not limited thereto. If the biologically active substance is a protein or an antibody, it may include any drug that binds specifically to a certain target in a cell, and the peptide can be introduced by fusion to the N-terminus or C-terminus of the protein or antibody.

In one embodiment, the biologically active substance may be contained in an amount that exhibits the highest effect. However, the content of the biologically active substance in the composition is particularly limited as long as the biologically active substance is delivered to a specific intracellular target. In one embodiment of the present invention, the biologically active substance and the stapled peptide may be contained in the composition at a molar ratio of 1:1 to 1:100, for example, 1:2 to 1:100, particularly 1:2 to 1:50. In an example of the present invention, it was shown that when siRNA and the stapled peptide were used at a specific molar ratio, for example, a molar ratio of 1:50, the siRNA significantly inhibited a target gene even when the concentration of the siRNA decreased.

In still another aspect, the present invention is directed to a method for preparing a stapled peptide, comprising the steps of: preparing a plurality of amino acids functionalized with double bond-containing compounds; and connecting at least two amino acids to each other by a reaction between the double bond-containing compounds of the amino acids arranged at predetermined positions.

The functionalized structure is not particularly limited, as long as it is a structure that can form the above-mentioned cyclic ring capable of connecting two or more groups to each other. For example, the functionalized structure enables amino acids having an alkenyl side-chain to be arranged at predetermined positions and to be connected to each other by a cyclic ring, thereby preparing a stapled peptide. The above-described constitutions of the present invention may also be applied to the preparation method in the same manner

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Preparation of Stapled Peptides

Figure 3:
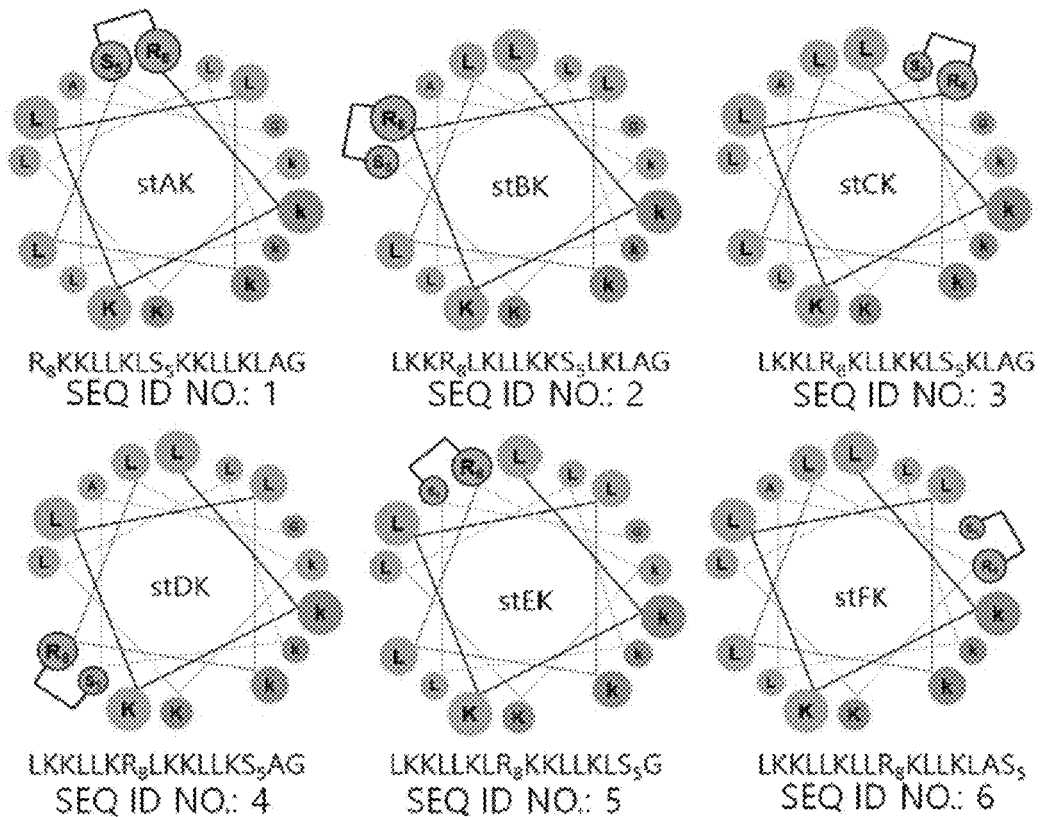
FIG. 3 shows a helical wheel representation of each staple peptide according to an example of the present invention and the sequence thereof.

From the hydrophobic amino acids of an alpha-helical peptide consisting of leucine and lysine residues, two amino acids at the i and i+7 positions were selected. The amino acid at the i position was substituted with (R)-2-(7'-octenyl)alanine, and the amino acid at the i+7 position was substituted with (S)-2-(4'-pentenyl)alanine, and ring closure metathesis was performed, thereby preparing hydrocarbon stapled peptides (FIG. 3). Table 1 below shows the amino acid sequence and name of each of the prepared peptides.

TABLE 1

| Name | Sequences[a] | SEQ ID NOs: |
|---|---|---|
| stAK | $R_8$KKLLKLS$_5$KKLLKLAG | 1 |
| stBK | LKKR$_8$LKLLKKS$_5$LKLAG | 2 |
| stCK | LKKLR$_8$KLLKKLS$_5$KLAG | 3 |
| stDK | LKKLLKR$_8$LKKLLKS$_5$AG | 4 |
| stEK | LKKLLKLR$_8$KKLLKLS$_5$G | 5 |
| stFK | LKKLLKLLR$_8$KLLKLAS$_5$ | 6 |
| LKH stEK | LKHLLHLR$_8$KHLLKLS$_5$G | 7 |
| Cys stEK | CLKKLLKLR$_8$KKLLKLS$_5$G | 8 |

[a]$R_8$: (R)-2-(7'-octenyl)alanine; $S_5$: (S)-2-(4'-pentenyl)alanine; the peptides of SEQ ID NOs: 1 to 7 contain amide at the C-terminus and acetyl at the N-terminus; the peptide of SEQ ID NO: 8 contains amide at the C-terminus and amine at the N-terminus.

Figure 5:
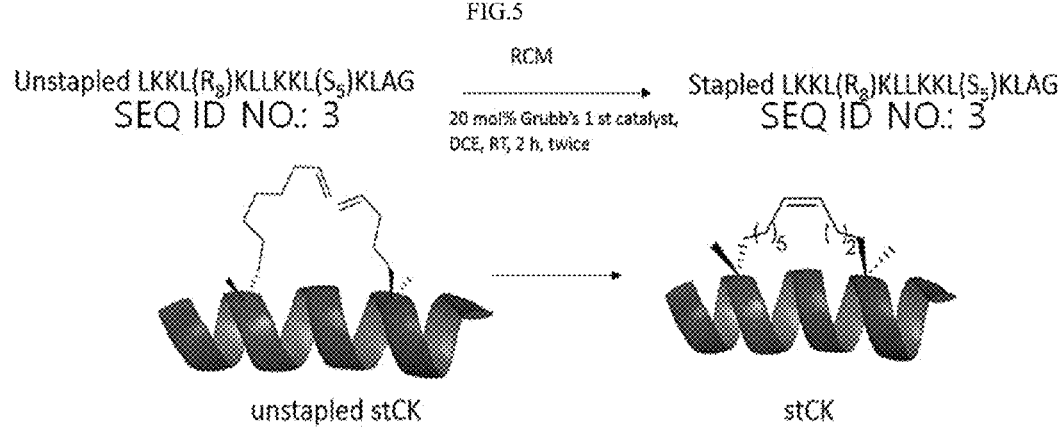
FIG. 5 is a schematic view showing a process of preparing a stapled peptide according to an example of the present invention.

Preparation of each stapled peptide was performed using ring closure metathesis (RCM) as shown in FIG. 5. An unstapled peptide was synthesized according to the standard Fmoc peptide synthesis method, and the RCM step was performed according to the above-mentioned reference. Briefly, a resin (30 μmol) having attached thereto a peptide having an N-terminal Fmoc protecting group was washed three times in each of carbon dichloride and acetylene dichloride for 1 minute each time. Then, the resin was treated with a solution of 1 ml of 6 mM Grubb's first generation catalyst in acetylene dichloride, and reacted at room temperature for 2 hours while it was bubbled with nitrogen gas. This reaction was repeated once more. After completion of the reaction, a reaction for attaching an acetyl functional group and attaching 5-TAMRA fluorescence was performed, and a stapled peptide was separated from the resin and purified by HPLC. A stapled peptide containing His or Cys was also synthesized in the same manner as described above, and the HPLC trace of each separated peptide is shown in FIGS. 7, 9a through 9e, 13 and 14.

The separated peptide was analyzed by MALDI-TOF mass spectrometry, and the results of the analysis are shown in FIGS. 8, 10a through 10e, 15 and 16. Ac stCK: MS [M+H]$^+$: 1927.4 (calcd) 1928.7 (obsd). 5-TAMRA stAK: MS [M+H]$^+$: 2298.5 (calcd) 2299.6 (obsd). 5-TAMRA stBK: MS [M+H]$^+$: 2298.5 (calcd) 2298.2 (obsd). 5-TAMRA stCK: MS [M+H]$^+$: 2298.5 (calcd) 2297.7 (obsd). 5-TAMRA stDK: MS [M+H]$^+$: 2298.5 (calcd) 2298.1 (obsd). 5-TAMRA stEK: MS [M+H]$^+$: 2340.6

(calcd) 2340.3 (obsd). LKH stEK: [M+H]⁺: 1996.32 (calcd), 1997.29 (obsd). Cys stEK [M+H]⁺: 2030.43 (calcd), 2030.75 (obsd).

Figure 6:
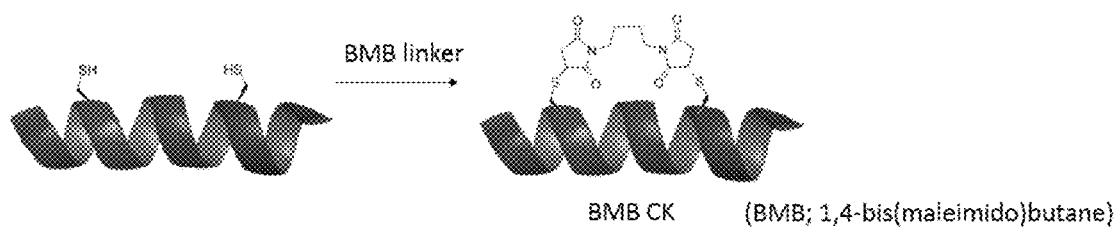
FIG. 6 is a schematic view showing a process of preparing a peptide comprising a BMB linker according to an example of the present invention.
Figure 7:
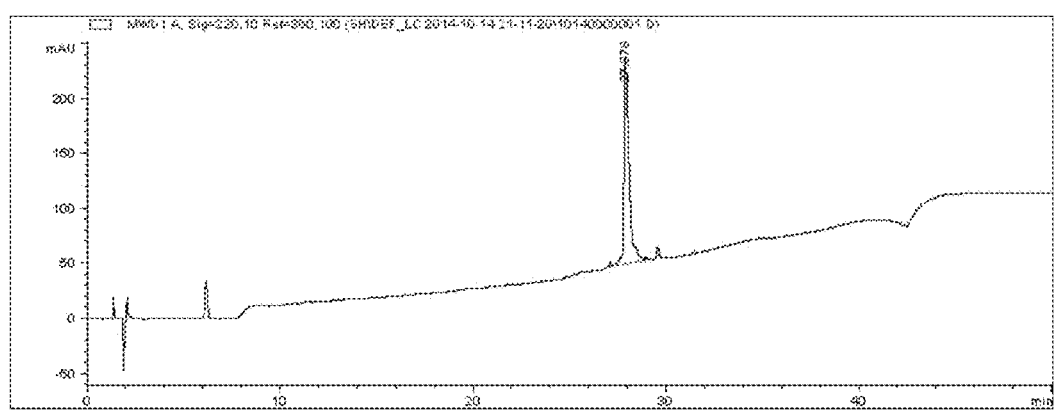
FIG. 7 shows the results of HPLC analysis of a stapled peptide (stCK) according to an example of the present invention.
Figure 8:
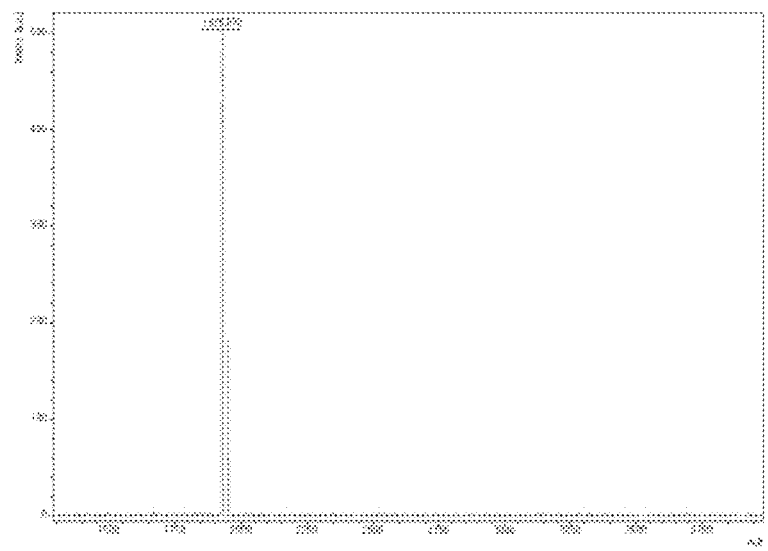
FIG. 8 shows the results of MALDI-TOF mass spectrometry of a stapled peptide (stCK) according to an example of the present invention.
Figure 9A:
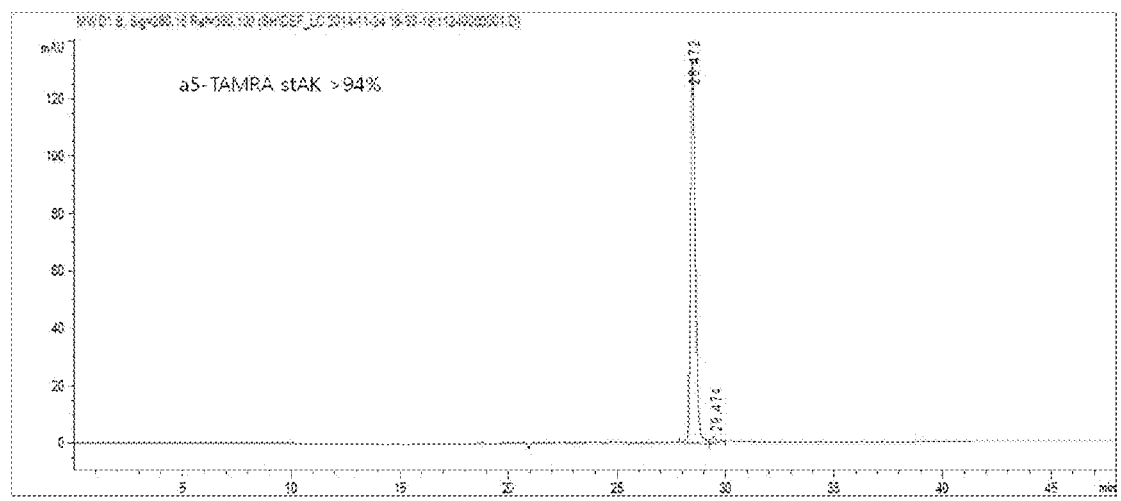
FIGS. 9a through 9e depict graphs showing the results of HPLC analysis of 5-TAMRA-labeled stapled peptides according to an example of the present invention. Specifically.
Figure 9B:
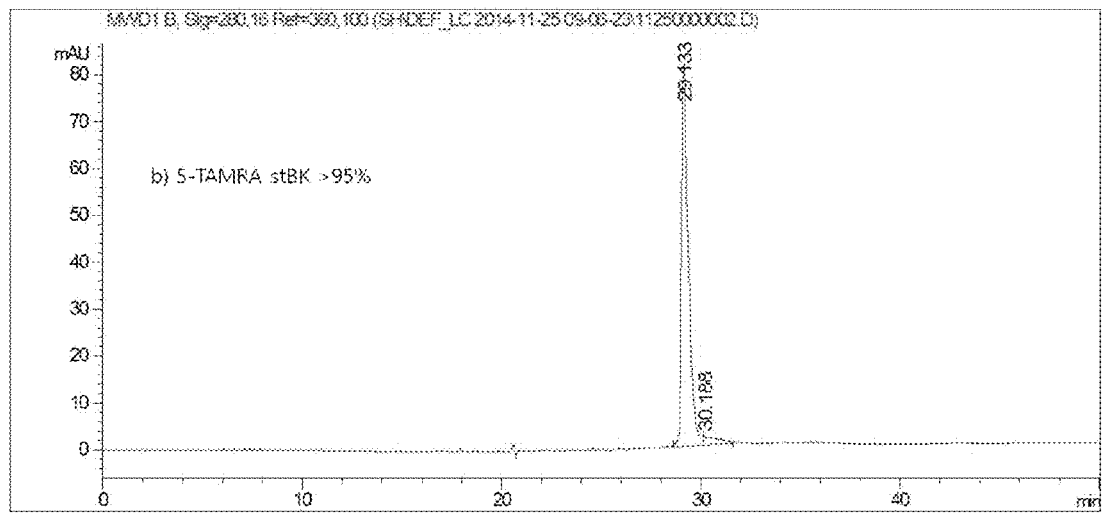
Figure 9C:
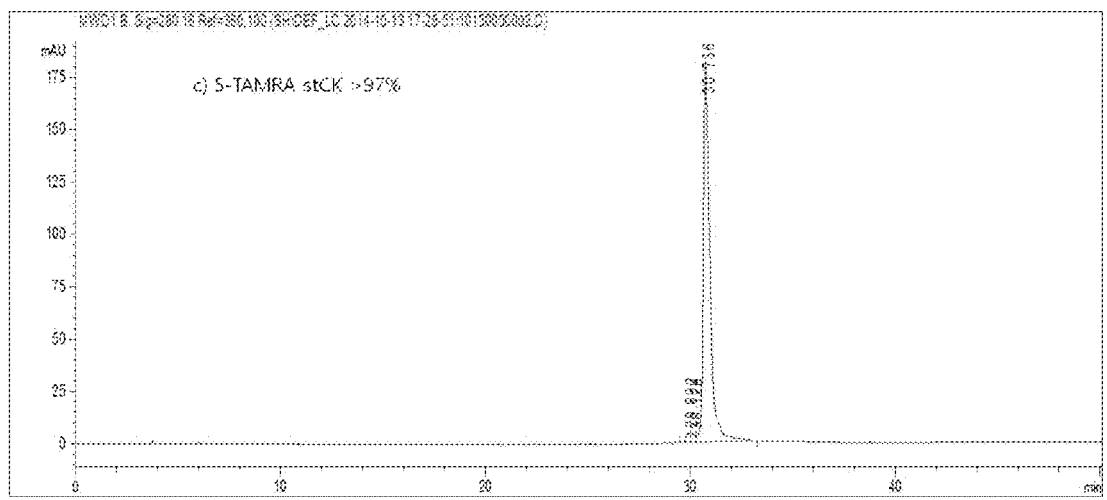
Figure 9D:
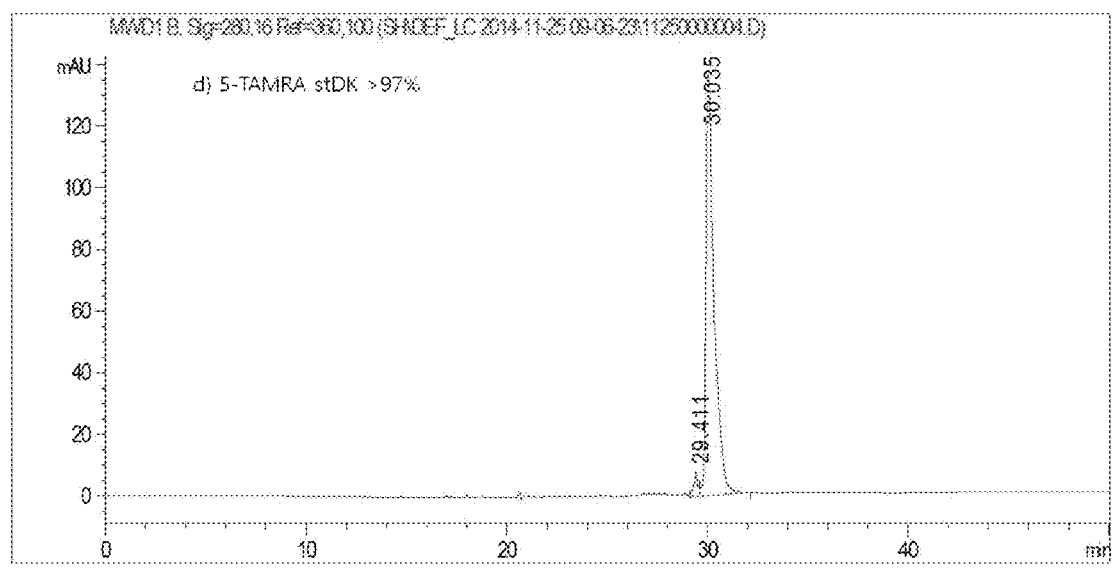
Figure 9E:
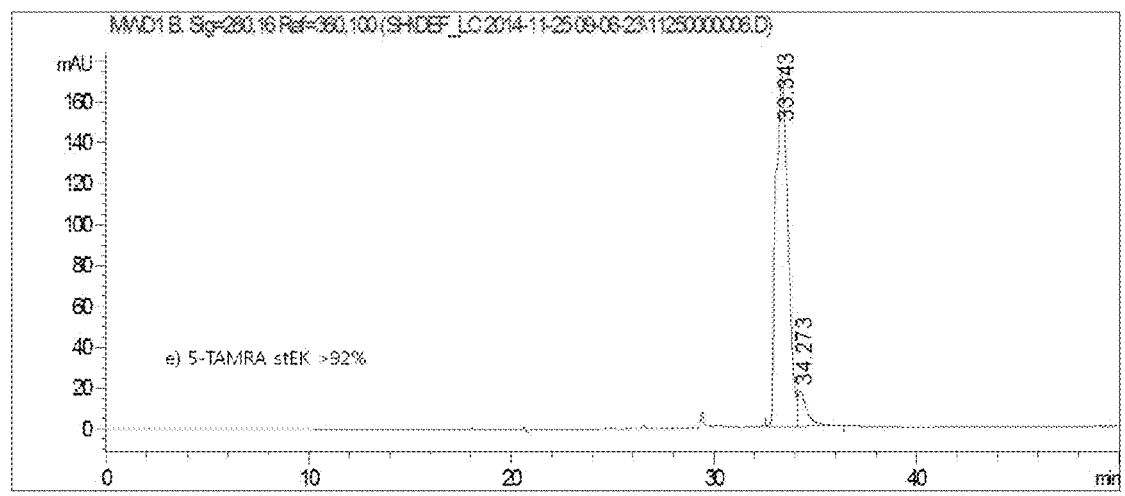
Figure 10A:
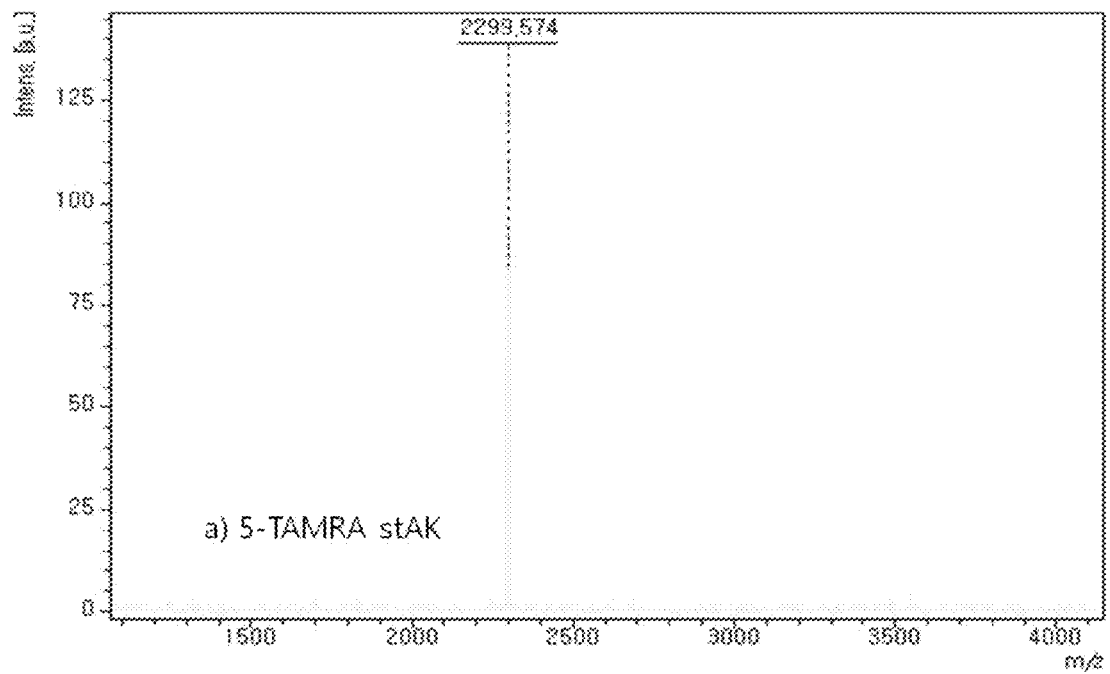
FIGS. 10a through 10e depict graphs showing the results of MALDI-TOF mass spectrometry of 5-TAMRA-labeled stapled peptides according to an example of the present invention. Specifically.
Figure 10B:
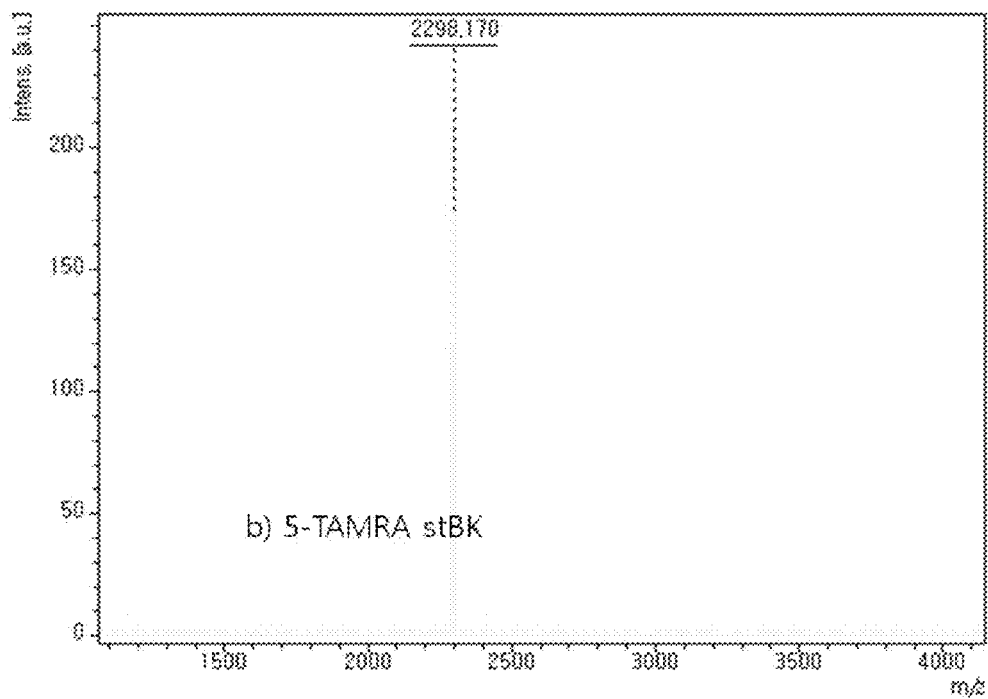
Figure 10C:
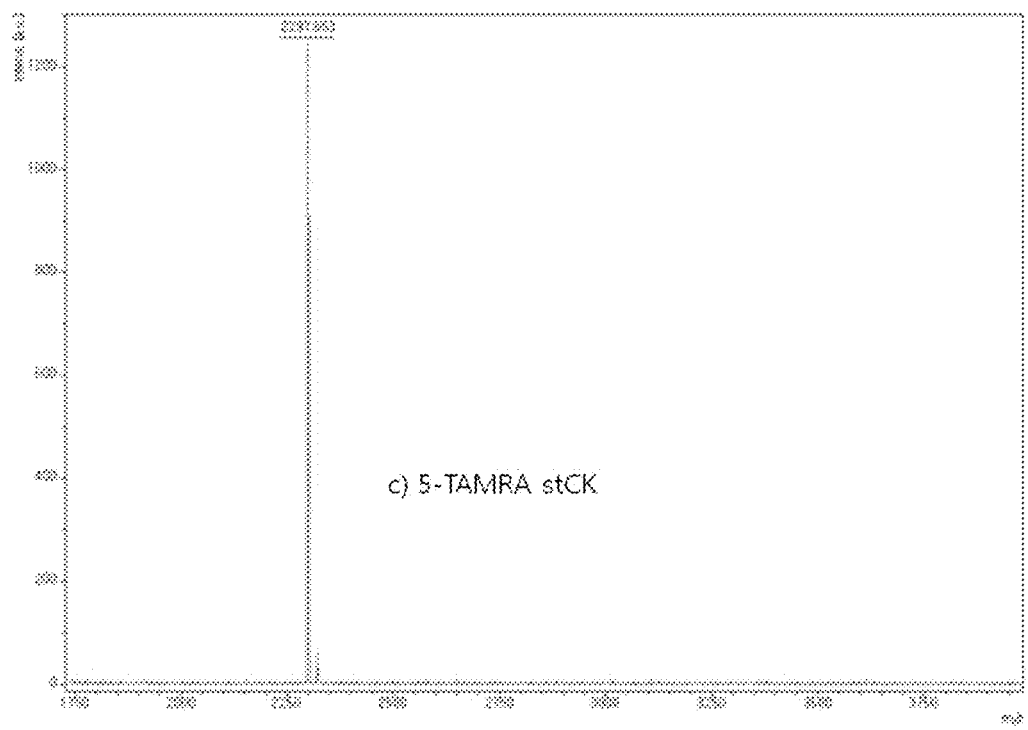
Figure 10D:
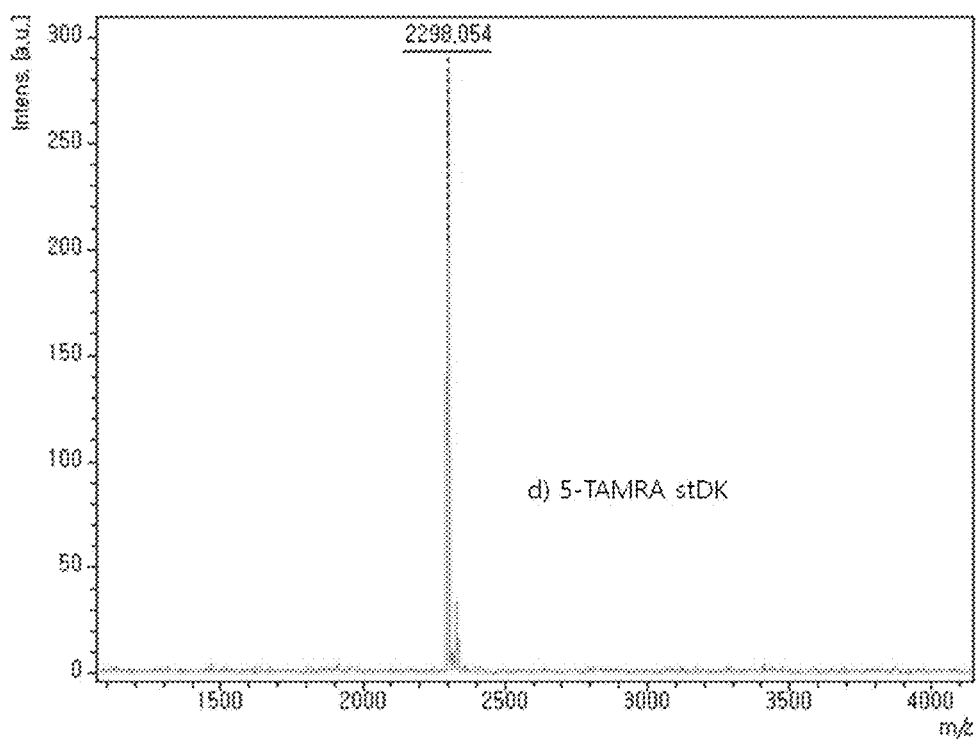
Figure 10E:
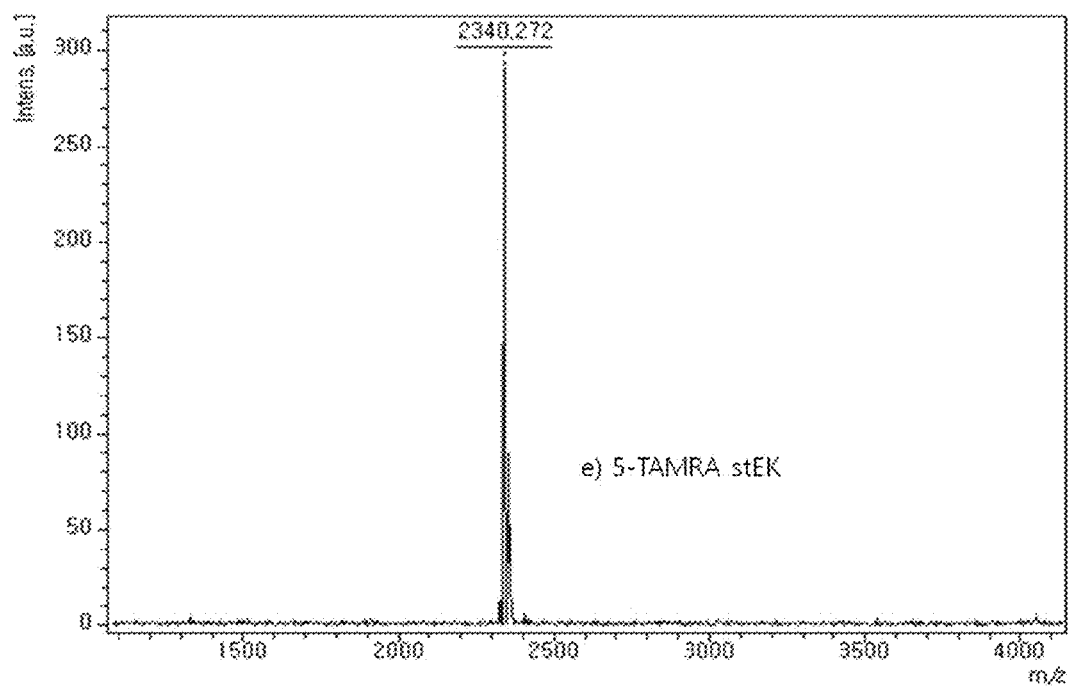
Figure 11:
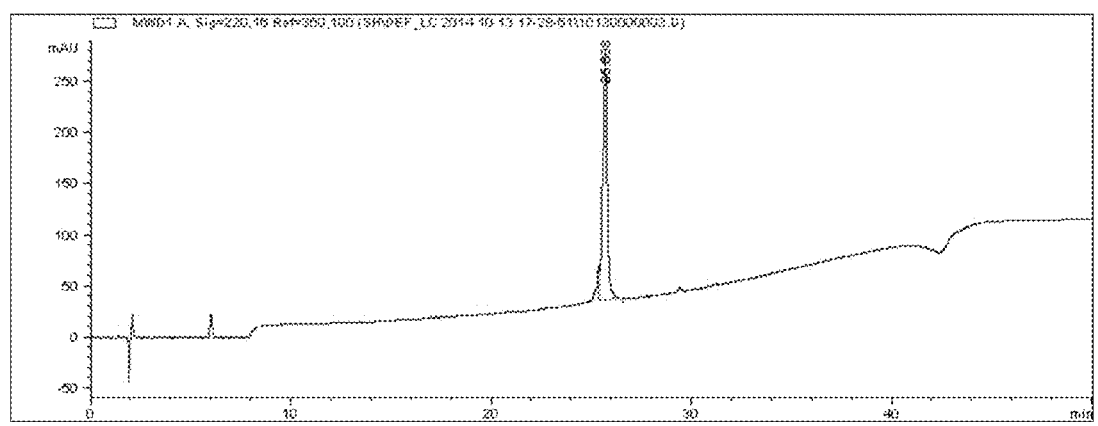
FIG. 11 is a graph showing the results of HPLC analysis of a peptide comprising a BMB linker (BMB CK) according to an example of the present invention.
Figure 12:
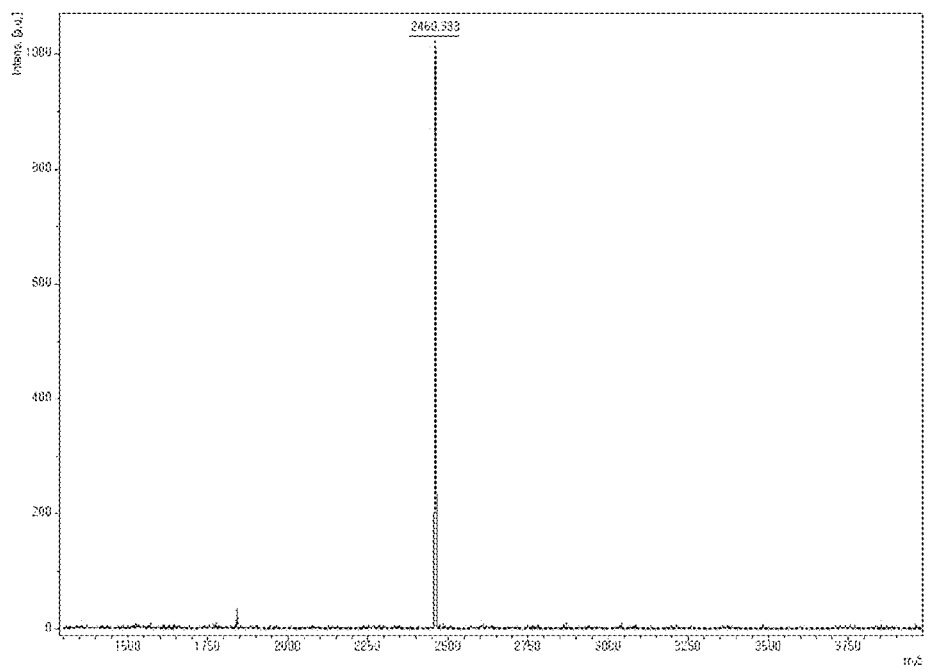
FIG. 12 is a graph showing the results of MALDI-TOF mass spectrometry of a peptide comprising a BMB linker (BMB CK) according to an example of the present invention.
Figure 13:
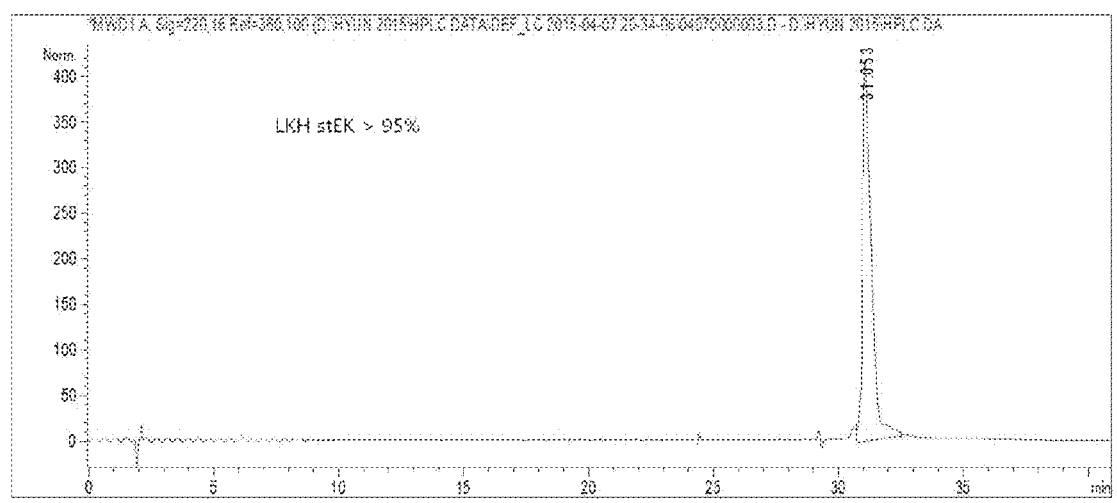
FIG. 13 is a graph showing the of HPLC analysis of a peptide containing His (LKH stEK) according to an example of the present invention.
Figure 14:
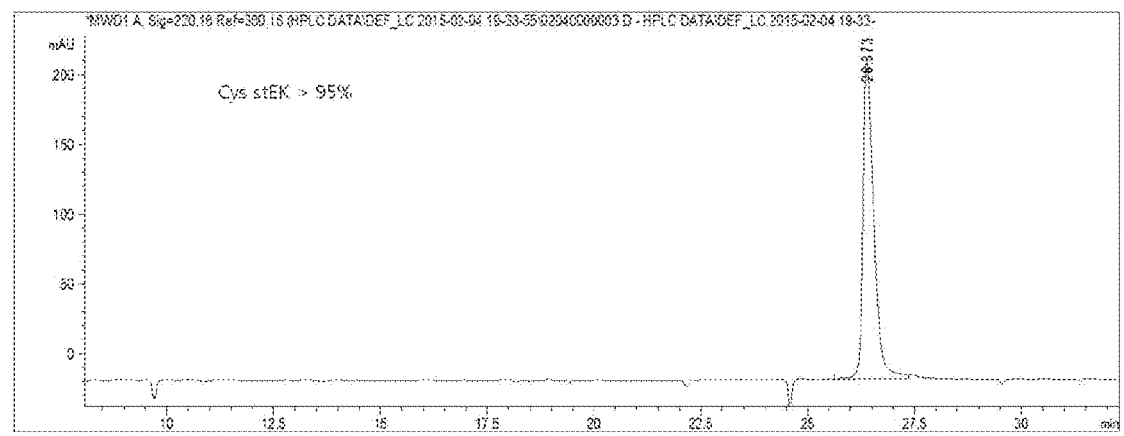
FIG. 14 is a graph showing the of HPLC analysis of a peptide containing Cys (Cys stEK) according to an example of the present invention.
Figure 15:
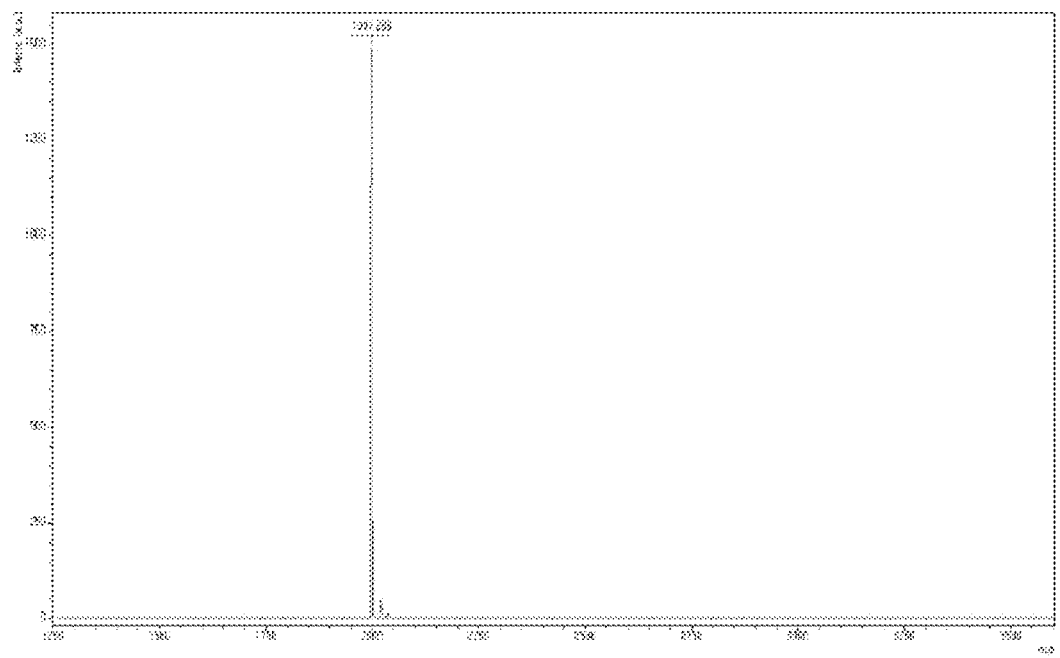
FIG. 15 is a graph showing the of MALDI-TOF mass spectrometry of a peptide containing His (LKH stEK) according to an example of the present invention.
Figure 16:
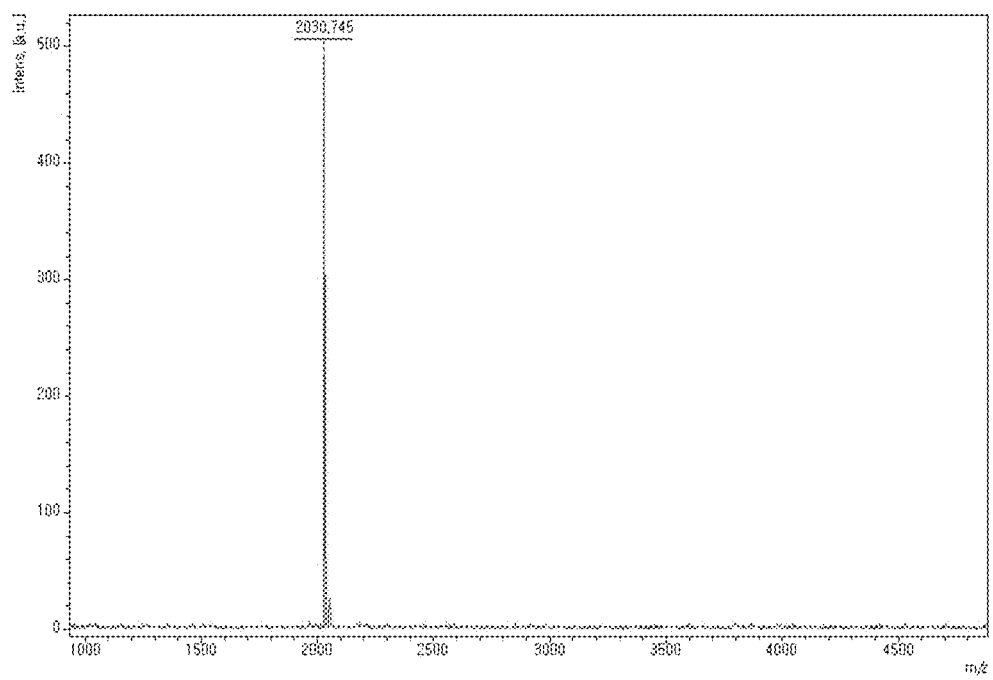
FIG. 16 is a graph showing the of MALDI-TOF mass spectrometry of a peptide containing Cys (LKH stEK) according to an example of the present invention.
Figure 17:
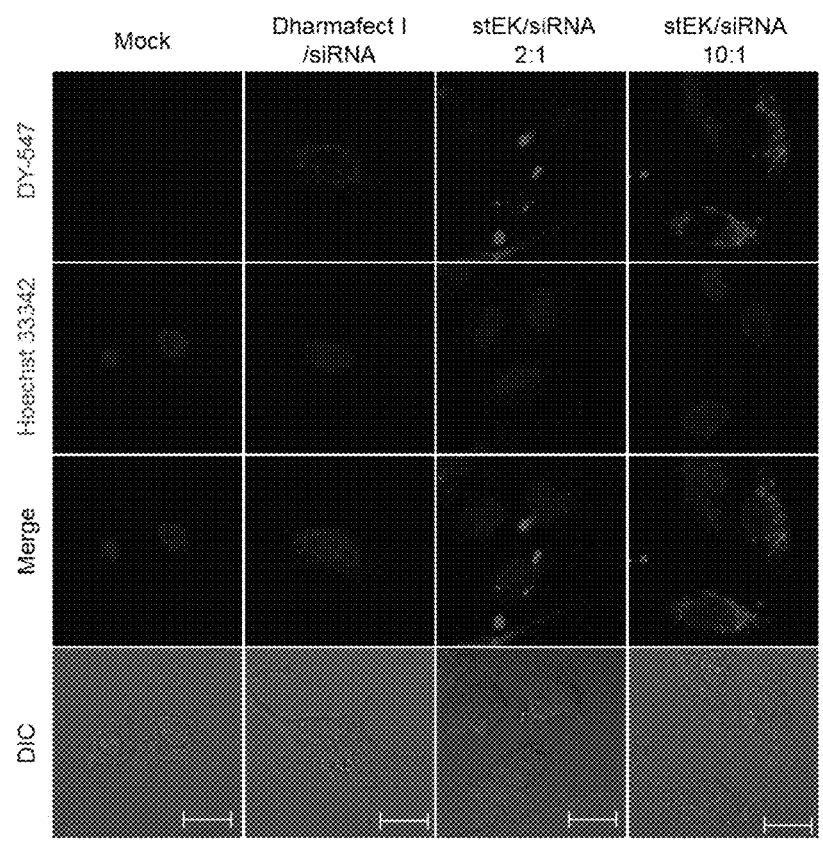
FIG. 17 shows the results obtained by delivering siRNA by use of a stapled peptide (stEK) according to an example of the present invention and observing the delivery of the siRNA with a fluorescence microscope.

As a control for the stapled peptide, a peptide comprising a BMB linker was prepared (FIG. 6). The amino acid sequence of this peptide was similar to that of stCK, and $R_8$ and $S_5$ in the peptide were substituted with cysteine. 5-TAMRA-BMB CK labeled with 5-TAMRA at the N-terminus was obtained by allowing the same amounts of the cysteine-containing peptide and 1,4-bis(maleimido)butane (BMB) to react in PBS buffer. The HPLC trace of the separated peptide is shown in FIG. 11. The separated peptide was analyzed by MALDI-TOF mass spectrometry, and the results of the analysis are shown in FIG. 12.

Example 2

Analysis of Cell-Penetrating Ability by FACS

Each of five 5-TAMRA-labeled stapled peptides, an amphipathic alpha-helical dimeric peptide (dimer CK) obtained in the previous patent, and a peptide comprising a BMB linker (BMB CK), was incubated with HeLa cells (the human cervical cancer cell line) at each concentration. In the results of the fluorescence activated cell sorting (FACS) experiment (FIGS. 2 and 4), the percentage of the fluorescent positive cells indicate that the cell-penetrating ability at all the concentrations used in the analysis increased in the order (FIG. 2: BMB CK<stCK<dimer CK).

Figure 2:
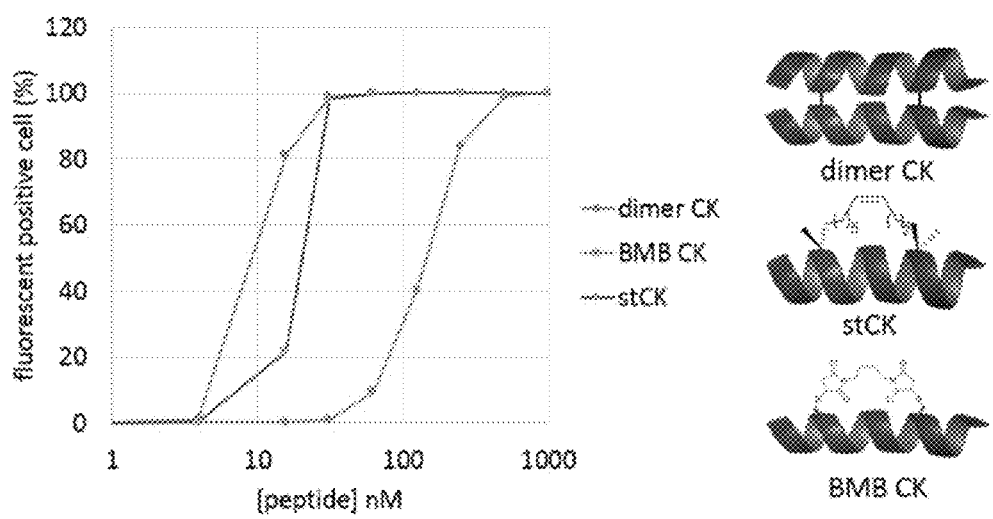
FIG. 2 shows the results of flow cytometry (FACS) performed to examine the cell-penetrating abilities of amphipathic alpha-helical stapled peptides according to an example of the present invention and a peptide comprising a BMB linker (left), and the structures of these peptides (right).

The stapled peptide (e.g., stCK) was labeled with the fluorescent dye 5-tetramethylrhodamine (5-TAMRA) and the cell-penetrating ability thereof was measured. As a result, it was shown that 90% or more of the cells contained the peptide at about 30 nM (FIG. 2).

For the amphipathic alpha-helical dimeric peptide (dimer CK) as described in PCT/KR2014/009778, it was shown that most of the cells contained the peptide at 10 nM, and that the stapled peptide (stCK) according to the present invention showed the same efficiency at about 30 nM.

Figure 4:
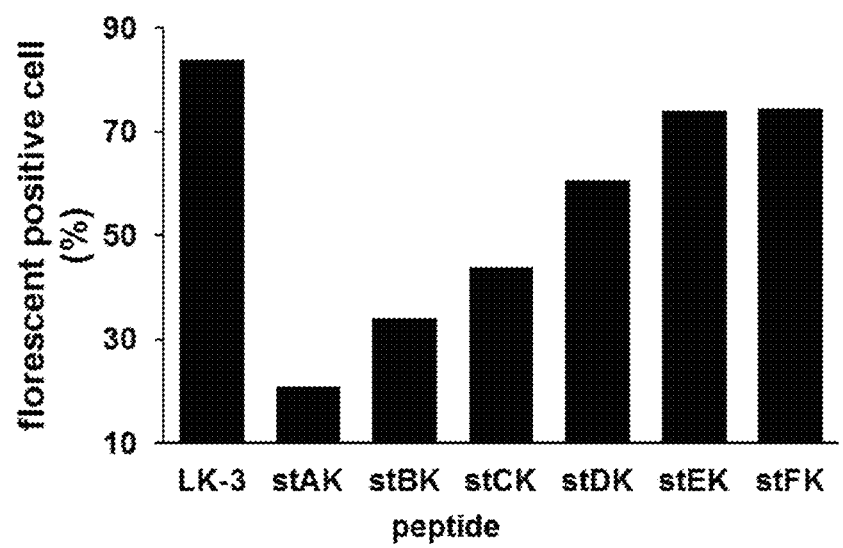
FIG. 4 shows the results of analyzing the cell-penetrating abilities of amphipathic alpha-helical stapled peptides according to an example of the present invention by flow cytometry (FACS) at the same concentration (16 nM).

Stapled peptides having substitutions at different positions were analyzed for their cell-penetrating ability at the same concentration (16 nM). As a result, it was shown that the percentage of the fluorescent positive cells increased in the order of st-AK<st-BK<st-CK<st-DK<st-EK. This suggests that the hydrocarbon linker position and amino acid sequence of the stapled peptide influence the cell-penetrating ability of the stapled peptide (FIG. 4).

However, the peptide having an increased alpha-helical content as a result of linking with a 1,4-bis(maleimido)butane (BMB) linker at the same amino acid position showed the same efficiency, when reaches to 500 nM. This suggests that the linker moiety plays an important role in the cell-penetrating ability, in addition to the assumption that the loss of entropy, which occurs in interactions during meeting with the cell membrane or proteins present in the cell membrane, in case of intracellular penetration, can be offset by a limited conformation, and that a high alpha-helical content contributes to high cell-penetrating ability. Herein, it appears that the linker of the hydrocarbon stapled peptide more contributes to the cell-penetrating ability than a hydrophilic linker such as BMB.

Example 3

Examination of siRNA Delivery Effect Using Fluorescence Microscope

HeLa cells (5×10⁴ cells/well) were grown on a 8-well Lab-tek chamber slide (Thermo Scientific). On the next day, the cells were transfected under the following conditions. siRNA (siGLO, GE life sciences) labeled with DY-547 was incubated with the stapled peptide stEK in PBS buffer at room temperature for 30 minutes, and then incubated with the cells in OptiMEM medium for 24 hours, followed by washing twice with PBS buffer. Next, the cells were imaged with a fluorescence microscope (Confocal LSM 710 system, Zeiss) and a fluorescence filter at a desired wavelength. As a result, it could be seen that, even when stEK and siRNA were mixed at a molar ratio of 2:1 or 10:1, delivery of the siRNA was efficiently achieved, like the case of Dharmafect I reagent used as a positive control.

Example 4

Examination of siRNA Delivery Effect Using Real-Time qPCR

Figure 18:
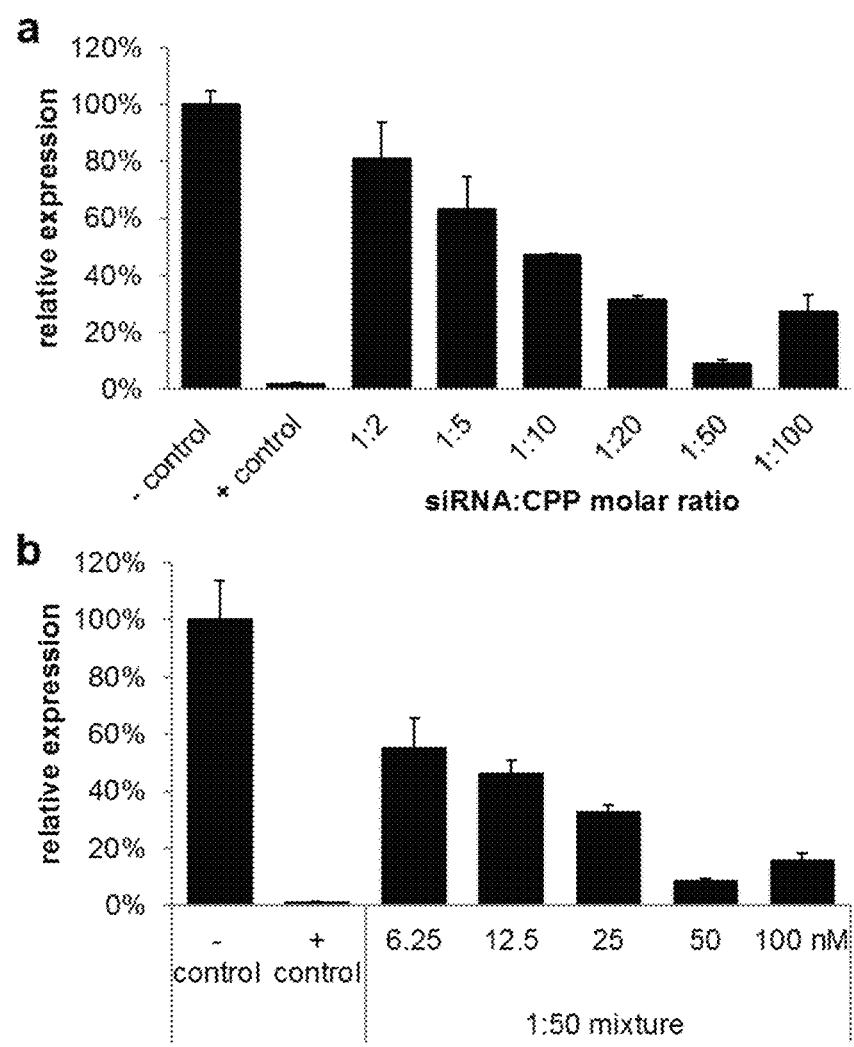
FIG. 18 shows the results obtained by delivering siRNA by use of a His-containing stapled peptide according to an example of the present invention and analyzing the expression level of a target RNA by RT-PCR.

HeLa cells (5 ×10⁴ cells/well) were grown on a 24-well plate. On the next day, the expression level of a target gene was analyzed using the His-containing stapled peptide LKH stEK and the siRNA siGenome (GE Life Sciences). Specifically, siRNA was used at a concentration of 50 nM and mixed in the ratios shown (graph a) in FIG. 18. The mixed siRNA was incubated with cells at that concentration for 24 hours, and then the expression level of the target mRNA was analyzed. As can be seen in FIG. 18 (graph a), when the siRNA was mixed with LKH stEK (which is CPP) at a molar ratio of 1:50, the siRNA most effectively inhibited the target gene. In addition, as shown in FIG. 18 (graph b), at a siRNA: CPP molar ratio of 1:50, the siRNA significantly inhibited the target gene even when the concentration of the siRNA further decreased.

Accordingly, it can be seen that the amphipathic alpha-helical stapled peptide of the present invention, which consists of lysine and leucine residues, has a significantly better ability to penetrate cells, compared to other peptide derivatives.

INDUSTRIAL APPLICABILITY

As described above, the amphipathic alpha-helical stapled peptide according to the present invention has a high ability to penetrate cells, and thus can effectively deliver a variety of physiologically active substances into cells.

It will be apparent to those skilled in the art to which the present invention pertains that various applications and modifications can be made based on the above description without departing from the scope of the present invention.

The invention claimed is:

1. A method for intracellular delivery of a biologically active substance, which comprises delivering a composition comprising an amphipathic alpha-helical stapled peptide comprising hydrophobic amino acids and hydrophilic amino acids, wherein the stapled peptide comprises any one of the following sequences:

X1KKLLKLX2KKLLKLAG, (SEQ ID NO: 1)

LKKX1LKLLKKX2LKLAG, (SEQ ID NO: 2)

LKKLX1KLLKKLX2KLAG, (SEQ ID NO: 3)

LKKLLKX1LKKLLKX2AG, (SEQ ID NO: 4)

LKKLLKLX1KKLLKLX2G, (SEQ ID NO: 5)

LKKLLKLLX1KLLKLAX2, (SEQ ID NO: 6)

LKHLLHLX1KHLLKLX2G, and (SEQ ID NO: 7)

CLKKLLKLX1KKLLKLX2G, (SEQ ID NO: 8)

wherein X1 is (R)-2-(7'-octenyl) alanine, and X2 is (S)-2-(4'-pentenyl) alanine.

2. The method of claim 1, wherein the stapled peptide further comprises cysteine at an N-terminus or C-terminus thereof.

3. The method of claim 1, wherein the biologically active substance is DNA, RNA, siRNA, an aptamer, a protein, an antibody, or a low-molecular weight compound.

4. The method of claim 1, wherein the biologically active substance and the stapled peptide are contained in the composition at a molar ratio of 1:2 to 1:100.

5. An amphipathic alpha-helical stapled peptide comprising any one of the following sequences:

X1KKLLKLX2KKLLKLAG, (SEQ ID NO: 1)

LKKX1LKLLKKX2LKLAG, (SEQ ID NO: 2)

LKKLX1KLLKKLX2KLAG (SEQ ID NO: 3)

LKKLLKX1LKKLLKX2AG, (SEQ ID NO: 4)

LKKLLKLX1KKLLKLX2G, (SEQ ID NO: 5)

LKKLLKLLX1KLLKLAX2, (SEQ ID NO: 6)

LKHLLHLX1KHLLKLX2G, and (SEQ ID NO: 7)

CLKKLLKLX1KKLLKLX2G, (SEQ ID NO: 8)

wherein X1 is (R)-2-(7'-octenyl) alanine, and X2 is (S)-2-(4'-pentenyl) alanine.

6. The amphipathic alpha-helical stapled peptide of claim 5, further comprising cysteine at an N-terminus or C-terminus of the peptide.

* * * * *

SEQUENCE LISTING

<160> NUMBER OF SEQ ID NOS: 8

<210> SEQ ID NO 1
<211> LENGTH: 16
<212> TYPE: PRT

```
<213> ORGANISM: Artificial Sequence
<220> FEATURE:
<223> OTHER INFORMATION: Stapled Peptide
<220> FEATURE:
<221> NAME/KEY: misc_feature
<222> LOCATION: (1)..(1)
<223> OTHER INFORMATION: Xaa can be any naturally occurring amino acid
      or (R)-2-(7'-octenyl) alanine
<220> FEATURE:
<221> NAME/KEY: misc_feature
<222> LOCATION: (8)..(8)
<223> OTHER INFORMATION: Xaa can be any naturally occurring amino acid
      or (S)-2-(4'-pentenyl) alanine

<400> SEQUENCE: 1

Xaa Lys Lys Leu Leu Lys Leu Xaa Lys Lys Leu Leu Lys Leu Ala Gly
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Stapled Peptide
<220> FEATURE:
<221> NAME/KEY: misc_feature
<222> LOCATION: (4)..(4)
<223> OTHER INFORMATION: Xaa can be any naturally occurring amino acid
      or (R)-2-(7'-octenyl) alanine
<220> FEATURE:
<221> NAME/KEY: misc_feature
<222> LOCATION: (11)..(11)
<223> OTHER INFORMATION: Xaa can be any naturally occurring amino acid
      or (S)-2-(4'-pentenyl) alanine

<400> SEQUENCE: 2

Leu Lys Lys Xaa Leu Lys Leu Leu Lys Lys Xaa Leu Lys Leu Ala Gly
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Stapled Peptide
<220> FEATURE:
<221> NAME/KEY: misc_feature
<222> LOCATION: (5)..(5)
<223> OTHER INFORMATION: Xaa can be any naturally occurring amino acid
      or (R)-2-(7'-octenyl) alanine
<220> FEATURE:
<221> NAME/KEY: misc_feature
<222> LOCATION: (12)..(12)
<223> OTHER INFORMATION: Xaa can be any naturally occurring amino acid
      or (S)-2-(4'-pentenyl) alanine

<400> SEQUENCE: 3

Leu Lys Lys Leu Xaa Lys Leu Leu Lys Lys Leu Xaa Lys Leu Ala Gly
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Stapled Peptide
<220> FEATURE:
<221> NAME/KEY: misc_feature
<222> LOCATION: (7)..(7)
<223> OTHER INFORMATION: Xaa can be any naturally occurring amino acid
      or (R)-2-(7'-octenyl) alanine
<220> FEATURE:
<221> NAME/KEY: misc_feature
```

```
<222> LOCATION: (14)..(14)
<223> OTHER INFORMATION: Xaa can be any naturally occurring amino acid
      or (S)-2-(4'-pentenyl) alanine

<400> SEQUENCE: 4

Leu Lys Lys Leu Leu Lys Xaa Leu Lys Lys Leu Leu Lys Xaa Ala Gly
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: stEK
<220> FEATURE:
<221> NAME/KEY: misc_feature
<222> LOCATION: (8)..(8)
<223> OTHER INFORMATION: Xaa can be any naturally occurring amino acid
      or (R)-2-(7'-octenyl) alanine
<220> FEATURE:
<221> NAME/KEY: misc_feature
<222> LOCATION: (15)..(15)
<223> OTHER INFORMATION: Xaa can be any naturally occurring amino acid
      or (S)-2-(4'-pentenyl) alanine

<400> SEQUENCE: 5

Leu Lys Lys Leu Leu Lys Leu Xaa Lys Leu Leu Lys Leu Xaa Gly
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: stFK
<220> FEATURE:
<221> NAME/KEY: misc_feature
<222> LOCATION: (9)..(9)
<223> OTHER INFORMATION: Xaa can be any naturally occurring amino acid
      or (R)-2-(7'-octenyl) alanine
<220> FEATURE:
<221> NAME/KEY: misc_feature
<222> LOCATION: (16)..(16)
<223> OTHER INFORMATION: Xaa can be any naturally occurring amino acid
      or (S)-2-(4'-pentenyl) alanine

<400> SEQUENCE: 6

Leu Lys Lys Leu Leu Lys Leu Leu Xaa Lys Leu Leu Lys Leu Ala Xaa
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: LKH stEK
<220> FEATURE:
<221> NAME/KEY: misc_feature
<222> LOCATION: (8)..(8)
<223> OTHER INFORMATION: Xaa can be any naturally occurring amino acid
      or (R)-2-(7'-octenyl) alanine
<220> FEATURE:
<221> NAME/KEY: misc_feature
<222> LOCATION: (15)..(15)
<223> OTHER INFORMATION: Xaa can be any naturally occurring amino acid
      or (S)-2-(4'-pentenyl) alanine

<400> SEQUENCE: 7

Leu Lys His Leu Leu His Leu Xaa Lys His Leu Leu Lys Leu Xaa Gly
1               5                   10                  15
```

```
-continued

<210> SEQ ID NO 8
<211> LENGTH: 17
<212> TYPE: PRT
<213> ORGANISM: Artificial Sequence
<220> FEATURE:
<223> OTHER INFORMATION: Cys stEK
<220> FEATURE:
<221> NAME/KEY: misc_feature
<222> LOCATION: (9)..(9)
<223> OTHER INFORMATION: Xaa can be any naturally occurring amino acid
      or (R)-2-(7'-octenyl) alanine
<220> FEATURE:
<221> NAME/KEY: misc_feature
<222> LOCATION: (16)..(16)
<223> OTHER INFORMATION: Xaa can be any naturally occurring amino acid
      or (S)-2-(4'-pentenyl) alanine

<400> SEQUENCE: 8

Cys Leu Lys Lys Leu Leu Lys Leu Xaa Lys Lys Leu Leu Lys Leu Xaa
1               5                   10                  15

Gly
```